(12) United States Patent
Qu et al.

(10) Patent No.: US 10,156,556 B2
(45) Date of Patent: Dec. 18, 2018

(54) METHOD FOR DETERMINING ECOLOGICAL RISKS OF POLYCYCLIC AROMATIC HYDROCARBON IN WATER BODY

(71) Applicant: Jiangsu Provincial Academy Of Environmental Science, Nanjing (CN)

(72) Inventors: Changsheng Qu, Nanjing (CN); Bing Li, Nanjing (CN); Haisuo Wu, Nanjing (CN); Shui Wang, Nanjing (CN)

(73) Assignee: JIANGSU PROVINCIAL ACADEMY OF ENVIRONMENTAL SCIENCE, Nanjing (CN)

( * ) Notice: Subject to any disclaimer, the term of this patent is extended or adjusted under 35 U.S.C. 154(b) by 290 days.

(21) Appl. No.: 14/773,502

(22) PCT Filed: Apr. 24, 2014

(86) PCT No.: PCT/CN2014/076122
§ 371 (c)(1),
(2) Date: Sep. 8, 2015

(87) PCT Pub. No.: WO2015/096321
PCT Pub. Date: Jul. 2, 2015

(65) Prior Publication Data
US 2016/0025698 A1    Jan. 28, 2016

(30) Foreign Application Priority Data
Dec. 24, 2013  (CN) .......................... 2013 1 0721931

(51) Int. Cl.
*G01N 33/18* (2006.01)

(52) U.S. Cl.
CPC ..... *G01N 33/1826* (2013.01); *G01N 33/1833* (2013.01); *Y02A 20/206* (2018.01)

(58) Field of Classification Search
CPC .... G06F 19/3431; G06Q 50/22; Y02W 30/95; C02F 2103/007
(Continued)

(56) References Cited

U.S. PATENT DOCUMENTS

| 8,721,785 B2 * | 5/2014 | Mohamed | C04B 2/005 106/716 |
| 2011/0173721 A1 * | 7/2011 | Albino | A24B 15/20 800/286 |

(Continued)

*Primary Examiner* — Jonathan Han
(74) *Attorney, Agent, or Firm* — Zhihua Han

(57) ABSTRACT

The present disclosure discloses a method for determining ecological risks of polycyclic aromatic hydrocarbon in a water body. The method may include (1) screening representative species of a water ecological system in a region; (2) obtaining toxicity data of benzoapyrene; (3) calculating benzoapyrene concentration values HC5 of 95% of species in the protected water ecological system; (4) determining types of polycyclic aromatic hydrocarbon pollutants and corresponding environmental concentrations thereof by sampling, and analyzing concentration distribution characteristics of various polycyclic aromatic hydrocarbons; (5) calculating ecological risk quotient values RQi of specific polycyclic aromatic hydrocarbon pollutants; and (6) calculating a total ecological risk quotient value RQt and confirming concrete ecological risks. The method may analyze whether potential risks caused by the polycyclic aromatic hydrocarbon pollutants are acceptable, and determine whether the total level of the ecological risks of the water body needs to be controlled.

2 Claims, 1 Drawing Sheet

(58) Field of Classification Search
USPC .................................................. 705/2; 702/20
See application file for complete search history.

(56) References Cited

U.S. PATENT DOCUMENTS

| | | | |
|---|---|---|---|
| 2012/0245858 A1* | 9/2012 | Carpenter | G01B 15/02 |
| | | | 702/28 |
| 2014/0188495 A1* | 7/2014 | Bi | G06Q 50/22 |
| | | | 705/2 |
| 2015/0100533 A1* | 4/2015 | Daulton | G06Q 10/10 |
| | | | 706/46 |

* cited by examiner

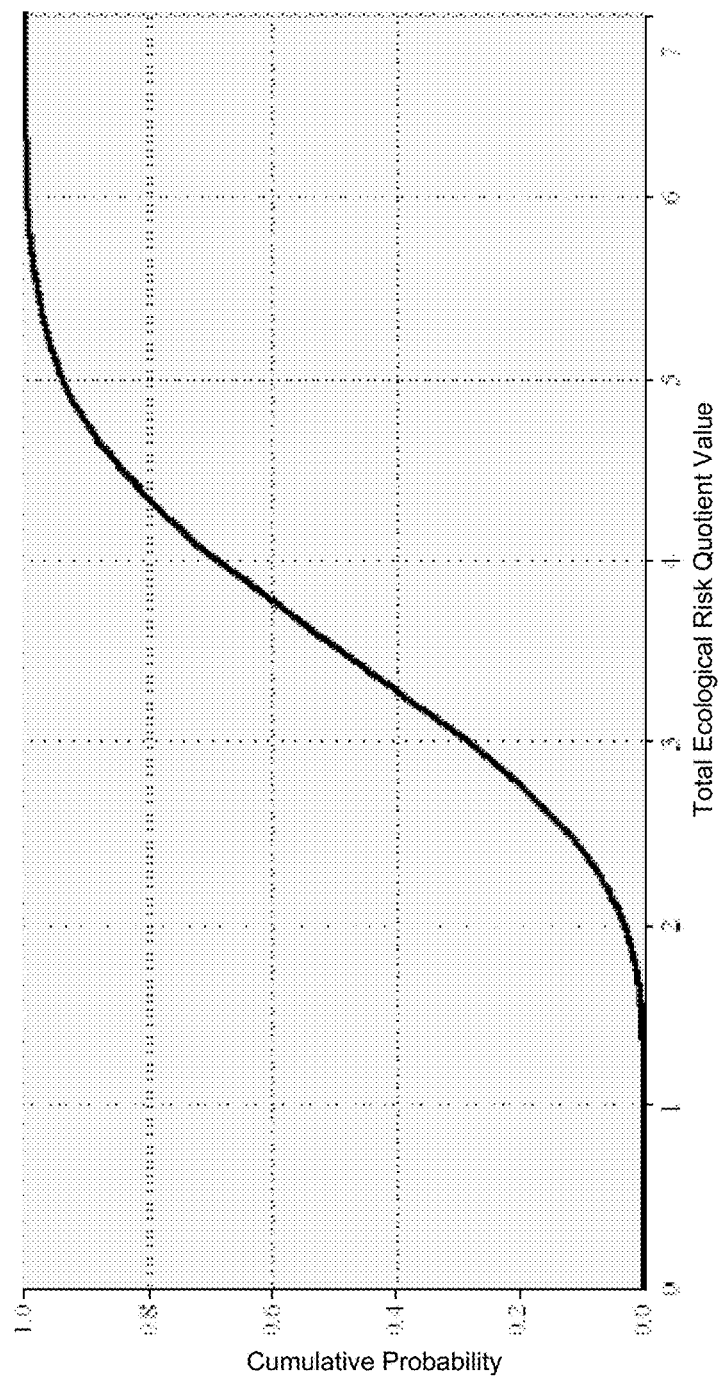

METHOD FOR DETERMINING ECOLOGICAL RISKS OF POLYCYCLIC AROMATIC HYDROCARBON IN WATER BODY

CROSS REFERENCE TO RELATED APPLICATION

This application is a national stage application of International application number PCT/CN 2014/076122, filed Apr. 24, 2014, titled "A METHOD FOR DETERMINING ECOLOGICAL RISKS OF POLYCYCLIC AROMATIC HYDROCARBON IN WATER BODY," which claims the priority benefit of Chinese Patent Application No. 2013107219316, filed on Dec. 24, 2013, which is hereby incorporated by reference in its entirety.

TECHNICAL FIELD

The present disclosure relates to a method for determining ecological risks, and more particularly, to a method for determining ecological risks of polycyclic aromatic hydrocarbons in a water body.

BACKGROUND

Polycyclic aromatic hydrocarbons are a kind of important environment pollutants, which are produced from such human activities as industrial technology process, anoxycausis, waste incineration and landfill, food preparation and traffic emmision and the like, and have widely existed in various environment mediums, such as a water body, and so on. The polycyclic aromatic hydrocarbon pollutants have the characters of carcinogenesis, teratogenesis, mutagenesis and non-biodegradability, which pose a threat to ecological system and human health, and therefore, more and more attentions are paid on pollution control and risk control of the polycyclic aromatic hydrocarbon pollutants.

Existing researches have shown that main rivers in China are contaminated by the polycyclic aromatic hydrocarbons at different levels. However, the water environment quality standard system in China does not cover the polycyclic aromatic hydrocarbon pollutants, and therefore, the basis for evaluating the pollution level of the polycyclic aromatic hydrocarbon in the water body is lacked. Internationally, the environment risk evaluation has become a research hotspot in the current environment field. In recent years, Chinese scholars have also tried to research on the water environment issue through environment risk theory and method, and provided a new thought for studying the ecological risks of polycyclic aromatic hydrocarbons in the water body.

At present, a quotient method is the most widely used in determining the ecological risks, i.e., the size of ecological risk is represented by means of a ratio of the environmental concentrations of pollutants to a reference value of toxicity. However, the calculation result of the quotient method belongs to a determined value, and is a rough estimate of risks. In fact, the concentration and space distribution of the polycyclic aromatic hydrocarbons in the water body have randomness and indeterminacy, and the ecological hazard effects thereof are also indeterminate due to the biological species and individual differences. Therefore, a scientific processing method will be the evaluation and analyzation of the ecological risks of the polycyclic aromatic hydrocarbons in the water body from the viewpoint of probability.

Moreover, since the basic toxicity data lacks limitation, the categories of the polycyclic aromatic hydrocarbons, the risks of which can be evaluated by using the quotient method, are limited, mainly focused on several minority polycyclic aromatic hydrocarbons like phenanthrene, anthracene, fluoranthene, pyrene, benz(a)anthracene, benzo[a]pyrene or the like, and researches on the ecological risks of other types of polycyclic aromatic hydrocarbons are relatively lacked. Meanwhile, due to similar structures and properties, different polycyclic aromatic hydrocarbon pollutants may produce cumulative risks. Therefore, the issue of cumulative risks of the polycyclic aromatic hydrocarbon pollutants shall also be considered while determining the ecological risks of polycyclic aromatic hydrocarbons in the water body.

A patent application 200910232672.4 (A Method for Determining Ecological Risks of Pesticides in Water Body) integrates the existing risk quotient method and the probability risk evaluation method, and uses relatively fewer toxicity data to achieve quantification of the total level of the ecological risks of pesticides in the water body. However, the final risk quotient values obtained through this method are still point estimated values, which do not solve the indeterminacy problem in the risk analysis procedure. Moreover, for the polycyclic aromatic hydrocarbon substances lacking toxicity data, the ecological risk analysis thereof cannot be performed in accordance with this method.

Generally speaking, the polycyclic aromatic hydrocarbon pollutants are research hotspots for scholars at home and abroad, but the scholars mainly concentrated on such aspects as migration and transformation and environmental fate thereof. In particular, there are fewer researches on risk identification of the water ecological system, and problems such as the indeterminacy during ecological risk analysis, determination for ecological risks of polycyclic aromatic hydrocarbon pollutants lacking toxicity data as well as united risks of different pollutants have not been solved yet. Presently, no mature literatures for solving the above problem of determining the ecological risks of polycyclic aromatic hydrocarbon in the water body are retrieved.

SUMMARY

1. Technical Problems to be Solved by the Present Disclosure

With respect to the incapable determination for the existing ecological risks due to the problems of depletion of the environmental standards for the polycyclic aromatic hydrocarbons in surface water and insufficient ecological environment supervision basis, the present disclosure establishes a method for determining ecological risks of polycyclic aromatic hydrocarbons in water body based on toxic equivalency factors and Monte Carlo simulation, which is applicable to the determination for pollution level and ecological risks of polycyclic aromatic hydrocarbons in the environmental water body.

2. Technical Solution

The disclosure employs the following technical solutions:

A method for determining ecological risks of polycyclic aromatic hydrocarbon in water body, includes the following steps of:

(1) screening representative species of a water ecological system in a region: in view of availability of local representative species and toxicity data thereof, comprising phytoplankton, zooplankton, insects and fishes, screening at least one from each species;

(2) obtaining toxicity data of benzoapyrene: collecting the chronic toxicity data of the benzoapyrene of the representative biological species, i.e., no observed effect concentration NOEC data;

(3) calculating benzoapyrene concentration values HC5 of 95% of species in the protected water ecological system: i.e., performing logarithmic transformation on the toxicity data and applying a formula $HC_5=\exp(X_m-K_L S_m)'$ to calculate, wherein m is the number of species, Xm means the arithmetic mean value of the toxicity data of the m species after the logarithmic transformation; Sm means the standard deviation of the toxicity data of the m species after the logarithmic transformation; and KL is a regulation factor, obtained from literature;

(4) determining types of polycyclic aromatic hydrocarbon pollutants in the region and corresponding environmental concentrations thereof by sampling, and analyzing concentration distribution characteristics of various polycyclic aromatic hydrocarbons;

(5) calculating ecological risk quotient values RQi of specific polycyclic aromatic hydrocarbon pollutants: calculating according to a formula $$RQ_i = \frac{EC_i \times TEF_i}{HC_5},$$

wherein ECi is the environmental concentration of an $i^{th}$ polycyclic aromatic hydrocarbon pollutant, TEFi is a toxic equivalency factor of the $i^{th}$ polycyclic aromatic hydrocarbon pollutant relative to the benzoapyrene, and a concrete numerical value is from literature, and HC5 is the benzoapyrene concentration values of 95% of species in the protected water ecological system; conducting random sampling for 10,000 times using a Monte Carlo sampling method according to the concentration distribution characteristics of different polycyclic aromatic hydrocarbons; and drawing cumulative probability distribution curves of the ecological risk quotient values of each polycyclic aromatic hydrocarbon pollutant according to the Monte Carlo sampling result, and analyzing the probability that the risk quotient values thereof RQi are no less than one; and (6) calculating the total ecological risk quotient value RQt of each polycyclic aromatic hydrocarbon pollutant: calculating according to a formula $$RQ_t = \sum RQ_i = \sum \frac{EC_i \times TEF_i}{HC_5},$$

and conducting random sampling for 10,000 times using the Monte Carlo sampling method according to the environmental concentration distribution characteristics of different polycyclic aromatic hydrocarbons; and drawing the cumulative probability distribution curve of the total ecological risk quotient value according to the Monte Carlo sampling result, thus determining the probability of the total ecological risk quotient value RQt greater than or equal to one, and confirming concrete ecological risks.

Risk management suggestions are formed according to the above results obtained: the polycyclic aromatic hydrocarbon pollutants are sorted according to the ecological risk quotient values RQi and the probability that the ecological risk quotient values RQi are no less than one, to determine a pollutant to be preferentially controlled; moreover, the sum of the ecological risk quotient values RQi of each polycyclic aromatic hydrocarbon pollutant is the total ecological risk quotient value RQt; and if a probability of the total ecological risk quotient value RQt of the polycyclic aromatic hydrocarbon pollutants in the evaluated water body greater than or equal to one is larger, which shows an ecological risk level caused by the polycyclic aromatic hydrocarbon pollutants to the water ecological system is higher, i.e., pollution discharge control is more needed, so as to weaken the damages caused by the polycyclic aromatic hydrocarbon pollutants to the water ecological system.

3. Advantageous Effects

The present disclosure provides a method for determining ecological risks of polycyclic aromatic hydrocarbon in water body, which solves the problem of indeterminacy during the process of ecological risk analysis through the integrated application of quotient method, toxic equivalency factors and Monte-Carlo simulation, and meanwhile enlarges the range of polycyclic aromatic hydrocarbon pollutants that can receive risk identification, and realizes the analysis of accumulative risks of different pollutants. Risk sorting is conducted based on the risk values of each polycyclic aromatic hydrocarbon pollutant to analyze whether potential risks caused by the polycyclic aromatic hydrocarbon pollutants are acceptable, and judge whether the total level of the ecological risks of the water body needs to be controlled, so as to provide scientific basis for the protection of water ecological system and the formulation of controlling measures of the polycyclic aromatic hydrocarbon pollution, and the like. The method can be widely applied to determine the pollution and ecological risk levels of the polycyclic aromatic hydrocarbon pollutants in the evaluated water body as well as preparation of corresponding ecological environment protective measures.

BRIEF DESCRIPTION OF THE DRAWINGS

FIG. 1 is a cumulative probability distribution diagram of total ecological risk of polycyclic aromatic hydrocarbons in a water body of a lake.

DETAILED DESCRIPTION OF THE PREFERRED EMBODIMENTS

The present disclosure will be further described in details hereinafter with reference to the drawings and embodiments.

Embodiment 1

Determining ecological risks of polycyclic aromatic hydrocarbon in a water body of a lake:

(1) Screening representative species of the lake: on the basis of investigating local species and considering the availability of corresponding toxicity data at the same time, six kinds of representative species are integrally selected, including green algae, chironomidae, *daphnia magna*, mussel, frog and barbel fish.

(2) Obtaining toxicity data of benzoapyrene: in PAN Pesticide Database and EPA EcoTox Database, the chronic toxicity data of benzoapyrene of the representative biological species is collected, as shown in Table 1.

(3) Calculating the benzoapyrene concentration values HC5 of 95% of species in the protected water ecological system: logarithmic transformation is performed on the toxicity data in Table 1 to obtain that the arithmetic mean value Xm 3.77 ug/L and the standard deviation Sm 4.95 ug/L, and calculation is conducted using a formula $HC_5=\exp(X_m-K_LS_m)i$, wherein the regulation factor KL is 1.81 (from published literature: Aldenberg and Slob, Confidence limits for hazardous concentrations based on logistically distributed NOEC toxicity data, 1991), and the HC5 value is obtained as 0.0056 ug/L.

(4) Determining varieties of polycyclic aromatic hydrocarbon pollutants in the water body of the lake and corresponding environmental concentrations thereof by sampling, and analyzing concentration distribution characteristics of various polycyclic aromatic hydrocarbons, as shown in Table 2.

(5) Calculating the ecological risk quotient values RQi of each polycyclic aromatic hydrocarbon pollutant: calculation is conducted according to a formula $$RQ_i = \frac{EC_i \times TEF_i}{HC_5},$$

wherein ECi is the environmental concentration of an $i^{th}$ polycyclic aromatic hydrocarbon pollutant, TEFi is a toxic equivalency factor of the $i^{th}$ polycyclic aromatic hydrocarbon pollutant relative to the benzoapyrene (from published literature: Nisbet ICT and Lagoy PK, Toxic equivalency factors (Tefs) for polycyclic aromatic-hydrocarbons, 1992, as shown in Table 3). Conducting random sampling for 10,000 times using a Monte Carlo sampling method according to the concentration distribution characteristics of different polycyclic aromatic hydrocarbons; drawing cumulative probability distribution curves of the ecological risk quotient values of each polycyclic aromatic hydrocarbon pollutant according to the Monte Carlo sampling result, wherein the results show that the risk quotient values of B[a]P and DBA from the sixteen kinds of polycyclic aromatic hydrocarbons are the highest, and the probability of the risk quotient values of B[a]P and DBA greater than or equal to one are respectively 54.4% and 61.8%, which show that the two pollutants cause potential ecological risks to the water body of the lake; and the probabilities of the risk quotient values of the rest polycyclic aromatic hydrocarbons greater than or equal to one are all zero.

(6) Calculating the total ecological risk quotient value RQt of each polycyclic aromatic hydrocarbon pollutant: calculation is conducted according to a formula $$RQ_i = \sum RQ_i = \sum \frac{EC_i \times TEF_i}{HC_5},$$

and random sampling is conducted for 10,000 times using the Monte Carlo sampling method according to the environmental concentration distribution characteristics of different polycyclic aromatic hydrocarbons; and the cumulative probability distribution curve of the total ecological risk quotient value is drawn according to the Monte Carlo sampling result (see FIG. 1). The results show that the average value of the total ecological risks caused by the polycyclic aromatic hydrocarbons in the water body of the lake is 3.3; by means of reading the numerical value of the Y-coordinate when the X-coordinate is 1, it is found that the probability of the risk quotient values greater than or equal to one is 99%, showing that the threatening probability of the polycyclic aromatic hydrocarbon pollutants to more than 5% of species in the water body of the lake is higher, which does not satisfy the demand of protecting 95% of species.

(7) Forming risk management suggestions: the probability of the risk quotient values of B[a]P and DBA from the sixteen kinds of polycyclic aromatic hydrocarbons in the water body of the lake greater than or equal to one are respectively 54.4% and 61.8%, which show that the respective ecological risks are high, and shall be considered as pollutants to be preferentially controlled. The probability of the total ecological risk quotient value caused by all the polycyclic aromatic hydrocarbons greater than or equal to one is 99%, showing that the ecological risks of the polycyclic aromatic hydrocarbon pollutants within the existing investigation time and region reflected by the existing chronic toxicity data is high, and the existing polycyclic aromatic hydrocarbon concentration level cannot protect 95% of species, and a pollution control measure needs to be formulated to protect the water ecological system of the lake.

TABLE 1

Toxicity Data of Benzoapyrene of Representative Species in a Lake

| Species name | Toxicity data type | Numerical value (ug/L) |
|---|---|---|
| Green algae | NOEC | 250000 |
| Chironomidae | NOEC | 5 |
| Daphnia magna | NOEC | 0.02 |
| Mussel | NOEC | 500 |
| Frog | NOEC | 10 |
| Barbel fish | NOEC | 54.2 |

TABLE 2

Concentration Value of Polycyclic Aromatic Hydrocarbon in Water Body of a Lake

| Pollutant name | Maximum | Minimum | Average value | Standard deviation |
|---|---|---|---|---|
| Nap | 5.48 | 0.23 | 2.09 | 1.41 |
| Acy | 0.71 | 0.05 | 0.28 | 0.23 |
| Ace | 3.10 | 0.13 | 0.93 | 0.79 |
| Flu | 4.26 | 0.13 | 1.75 | 1.15 |
| Phe | 11.76 | 0.27 | 2.62 | 2.68 |
| Ant | 2.56 | 0.16 | 0.79 | 0.60 |
| Flt | 3.22 | 0.03 | 0.44 | 0.68 |
| Pyr | 2.38 | 0.03 | 0.32 | 0.53 |
| B[a]A | 0.47 | 0.01 | 0.05 | 0.10 |
| Chr | 0.81 | 0.01 | 0.12 | 0.18 |
| B[b]F | 0.50 | 0.02 | 0.19 | 0.14 |
| B[k]F | 0.17 | 0.01 | 0.05 | 0.04 |
| B[a]P | 0.16 | 0.01 | 0.05 | 0.04 |
| DBA | 0.15 | 0.01 | 0.06 | 0.04 |
| Ind | 0.13 | 0.01 | 0.04 | 0.04 |
| B[ghi]P | 0.53 | 0.01 | 0.14 | 0.14 |

TABLE 3

Toxic Equivalency Factor of Polycyclic Aromatic Hydrocarbon Pollutant Relative to Benzoapyrene

| Pollutant name | Toxic equivalency factor |
|---|---|
| Nap | 0.001 |
| Acy | 0.001 |
| Ace | 0.001 |
| Flu | 0.001 |
| Phe | 0.001 |
| Ant | 0.01 |
| Flt | 0.001 |
| Pyr | 0.001 |
| B[a]A | 0.1 |
| Chr | 0.01 |
| B[b]F | 0.1 |

TABLE 3-continued

Toxic Equivalency Factor of Polycyclic Aromatic
Hydrocarbon Pollutant Relative to Benzoapyrene

| Pollutant name | Toxic equivalency factor |
| --- | --- |
| B[k]F | 0.1 |
| B[a]P | 1 |
| DBA | 1 |
| Ind | 0.1 |
| B[ghi]P | 0.01 |

What is claimed is:

1. A method for determining ecological risks of polycyclic aromatic hydrocarbon in a water bodyriver, the method comprising:
   (1) screening species of a water ecological system in a region based on availability of local representative species and toxicity data thereof to obtain representative species comprising at least one species of each of phytoplankton, zooplankton, insects and fishes;
   (2) obtaining toxicity data of benzoapyrene by collecting chronic toxicity data of the benzoapyrene of the representative species or non-observed effect concentration NOEC data;
   (3) calculating benzoapyrene concentration values $HC_5$ of about 95% of species in the water ecological system by performing logarithmic transformation on the toxicity data and applying a formula $HC_5 = \exp(X_m - K_L S_m)'$, wherein the m is a number of species, the $X_m$ represents an arithmetic mean value of the toxicity data of the m species after the logarithmic transformation, the $S_m$ represents the standard deviation of the toxicity data of the m species after the logarithmic transformation, and the $K_L$ is a regulation factor obtained from literature;
   (4) determining types of polycyclic aromatic hydrocarbon pollutants in the region and corresponding environmental concentrations thereof by sampling and analyzing concentration distribution characteristics of various polycyclic aromatic hydrocarbons;
   (5) calculating ecological risk quotient values RQi of specific polycyclic aromatic hydrocarbon pollutants by calculating according to a formula $$RQ_i = \frac{EC_i \times TEF_i}{HC_5},$$

wherein the ECi is the environmental concentration of an $i^{th}$ polycyclic aromatic hydrocarbon pollutant, the TEFi is a toxic equivalency factor of the $i^{th}$ polycyclic aromatic hydrocarbon pollutant relative to the benzoapyrene, and a concrete numerical value is from literature, and the $HC_5$ is the benzoapyrene concentration values of 95% of species in the protected water ecological system; thereof conducting random sampling for 10,000 times using a Monte Carlo sampling method according to the concentration distribution characteristics of different polycyclic aromatic hydrocarbons; drawing cumulative probability distribution curves of the ecological risk quotient values of each polycyclic aromatic hydrocarbon pollutant according to a Monte Carlo sampling result; and analyzing a probability that the risk quotient values thereof RQi are no less than one, a larger probability showing a higher ecological risk caused by the polycyclic aromatic hydrocarbon pollutant in the evaluated water body; and
   (6) calculating the total ecological risk quotient value RQt of each polycyclic aromatic hydrocarbon pollutant by calculating according to a formula $$RQ_t = \sum RQ_i = \sum \frac{EC_i \times TEF_i}{HC_5},$$

and conducting random sampling for 10,000 times using the Monte Carlo sampling method according to the environmental concentration distribution characteristics of different polycyclic aromatic hydrocarbons; thereof drawing the cumulative probability distribution curve of the total ecological risk quotient value according to the Monte Carlo sampling result, and determining the probability of the total ecological risk quotient value RQt greater than or equal to one, and confirming concrete ecological risks.

2. The method of claim 1, wherein the polycyclic aromatic hydrocarbon pollutants are sorted according to the ecological risk quotient values $Rq_i$, wherein a pollutant with the probability of the ecological risk quotient values $RQ_i$ greater than or equal to one is preferentially controlled, and wherein a larger probability of the total ecological risk quotient value RQt of the polycyclic aromatic hydrocarbon pollutants in the evaluated water body greater than or equal to one indicates that a higher ecological risk level is caused by the polycyclic aromatic hydrocarbon pollutants to the water ecological system or more necessarily pollution discharge control is performed to weaken damages caused by the polycyclic aromatic hydrocarbon pollutants to the water ecological system.

* * * * *